United States Patent
Bettsworth et al.

(10) Patent No.: US 9,606,120 B2
(45) Date of Patent: Mar. 28, 2017

(54) INTERFERING PEPTIDES AND METHOD FOR DETECTING MICROORGANISMS

(71) Applicant: BIOMÉRIEUX, Marcy L'Etoile (FR)

(72) Inventors: Florence Bettsworth, Dommartin (FR); Catherine Pothion, Lyons (FR); Béatrice Seigneres, Genas (FR)

(73) Assignee: BIOMERIEUX, Marcy L'Etoile (FR)

( * ) Notice: Subject to any disclaimer, the term of this patent is extended or adjusted under 35 U.S.C. 154(b) by 0 days.

(21) Appl. No.: 14/380,790

(22) PCT Filed: Mar. 11, 2013

(86) PCT No.: PCT/FR2013/050504
§ 371 (c)(1),
(2) Date: Aug. 25, 2014

(87) PCT Pub. No.: WO2013/132198
PCT Pub. Date: Sep. 12, 2013

(65) Prior Publication Data
US 2015/0024380 A1    Jan. 22, 2015

(30) Foreign Application Priority Data
Mar. 9, 2012 (FR) ..................................... 12 52142

(51) Int. Cl.
| | | |
|---|---|---|
| *C12N 15/85* | (2006.01) | |
| *A61K 38/00* | (2006.01) | |
| *A61K 48/00* | (2006.01) | |
| *C07H 21/04* | (2006.01) | |
| *C07K 14/47* | (2006.01) | |
| *G01N 33/569* | (2006.01) | |
| *G01N 33/53* | (2006.01) | |
| *G01N 33/543* | (2006.01) | |

(52) U.S. Cl.
CPC ... *G01N 33/56983* (2013.01); *G01N 33/5306* (2013.01); *G01N 33/54393* (2013.01); *G01N 33/56911* (2013.01); *G01N 2469/10* (2013.01)

(58) Field of Classification Search
CPC .. A61K 31/7115; A61K 38/00; A61K 48/005; A61K 48/0066; C07K 14/535
See application file for complete search history.

(56) References Cited

U.S. PATENT DOCUMENTS

| | | | |
|---|---|---|---|
| 4,931,385 A | | 6/1990 | Block et al. |
| 5,674,676 A | * | 10/1997 | Seidel et al. ............... 435/5 |
| 6,153,393 A | * | 11/2000 | Seidel ............... G01N 33/5306 435/69.3 |

FOREIGN PATENT DOCUMENTS

| | | |
|---|---|---|
| DE | 4240980 A1 | 2/1994 |
| EP | 0260903 A2 | 3/1988 |
| EP | 0484787 A2 | 5/1992 |
| EP | 0525916 A1 | 2/1993 |
| EP | 0582243 A2 | 2/1994 |
| EP | 0922958 A2 | 6/1999 |
| WO | 2008027942 A2 | 3/2008 |
| WO | WO2008027942 * | 3/2008 |

OTHER PUBLICATIONS

Dandekar et al., "Re-annotating the *Mycoplasma pneumoniae* genome sequence: adding value, function and reading frames", 2000, Nucleic Acids Research, 28(17):3278-3288.*
Blick, "Challenges in immunoassay standardization", 2010, 19(20):pdf pp. 1-3.*
Aug. 9, 2013 Written Opinion of the International Searching Authority issued in International Application No. PCT/FR2013/050504.
Aug. 9, 2013 International Search Report issued in International Application No. PCT/FR2013/050504.
Chevalier et al., "Biotin and Digoxigenin as Labels for Light and Electron Microscopy in Situ Hybridization Probes: Where Do We Stand?," The Journal of Histochemistry & Cytochemistry, vol. 45, pp. 481-491, 1997.
Kricka, Larry, "Human Anti-Animal Antibody Interferences in Immunological Assays," Clinical Chemistry, vol. 45, pp. 942-956, 1999.
Fields et al., "Solid Phase Peptide Synthesis Utilizing 9-Fluorenylmethoxycarbonyl Amino Acids," International J. Peptide Protein Res., vol. 35, pp. 161-214, 1990.
Merrifield, R.B., "Solid Phase Peptide Synthesis. I. The Synthesis of a Tetrapeptide," vol. 85, pp. 2149-2154, 1963.
Ng et al., "Predicting Deleterious Amino Acid Substitutions," Genome Research, vol. 11, pp. 863-874, 2001.
Tate et al., "Interferences in Immunoassay," Clin Biochem Rev. vol. 25, pp. 105-120, 2004.

* cited by examiner

Primary Examiner — Janet L Andres
Assistant Examiner — Barry A Chestnut
(74) *Attorney, Agent, or Firm* — Oliff PLC

(57) ABSTRACT

The invention relates to novel interfering peptides having peptide sequence S with between 7 and 12 amino acids, originating from the peptide sequence of an antigenic protein of a micro-organism M, the sequence S being aligned with a peptide sequence S' with between 7 and 12 amino acids originating from the peptide sequence of a target protein of a micro-organism M' that is different from the micro-organism M, provided that: sequences S and S' have at least 50% identity over their length of 7 to 12 amino acids and at least 4 identical or analogous contiguous amino acids; and their length is identical or they have 1 or 2 different amino acids distributed at one and/or the other end of the sequences. The invention also relates to a method for the in vitro immunoassay-based detection of the presence of a micro-organism M' or M in a biological sample.

20 Claims, 1 Drawing Sheet

Figure 1

| | | | |
|---|---|---|---|
| Y7E-1 | YSPTHYVPE | (SEQ°ID :1) | *Staphylococcus aureus* |
| V7E | V....... | (SEQ°ID :2) | HCV |

Figure 2

A

| | | | |
|---|---|---|---|
| A8E | AQKRLAPYIE | (SEQ°ID :3) | *Streptococcus pneumoniae* |
| E8E | ECSQH.-... | (SEQ°ID :4) | HCV |

B

| | | | |
|---|---|---|---|
| Y7E-2 | YFQHIPYLE | (SEQ°ID :5) | *Bacillus subtilis* |
| E8E | ECS..L..I. | (SEQ°ID :4) | HCV |

C

| | | | |
|---|---|---|---|
| D8E | DIDAVLPYIE | (SEQ°ID :6) | *Pseudomonas entomophila* ou *putida* |
| E8E | ECSQH..... | (SEQ°ID :4) | HCV |

Figure 3

| | | | |
|---|---|---|---|
| E8L-1 | EAYRKEQQLL | (SEQ°ID :7) | *Mycoplasma pneumoniae* |
| E8L-2 | .R.L.D.... | (SEQ°ID :8) | HIV |

Figure 4

| | | | |
|---|---|---|---|
| E8E | ECSQHLPYIE | (SEQ°ID :4) | HCV |
| A6M | A....KGM | (SEQ°ID :9) | *Streptococcus pneumoniae* |

INTERFERING PEPTIDES AND METHOD FOR DETECTING MICROORGANISMS

The present invention relates to the diagnostic field. In particular, it relates to novel peptides which are particularly useful for eliminating interference problems in the context of the in vitro immunological assay-based detection of the presence of a microorganism in a biological sample, the interference problems being linked to the sample tested.

Immunological assay-based detection methods are widely used in the diagnostic field. These methods make it possible to detect analytes in the form of proteins (antigens/antibodies), of peptides and of haptens, for instance steroids or vitamins. The immunological assay, also known as immunoassay method or immunoenzymatic test, is a method widely known to those skilled in the art, involving immunological reactions between the analyte to be detected and one or more partner(s) for binding to this analyte. By way of example of such immunoassay methods, mention may be made of methods such as ELISA, ELFA, CLIA, ECLIA, IRMA and RIA which can operate according to the "sandwich" principle, or else according to the "competition" principle, and immunodetection methods, for instance immunohistochemistry, immunocytochemistry, immunofluorescence, Western blot and Dot blot.

The results of these immunological assays are then supplied by laboratory to a practitioner who will interpret them in order to diagnose a pathological state and subsequently provide the patient with an appropriate treatment. It is therefore particularly important for these assays to be both highly sensitive, in the sense that they do not give false-negative results, and highly specific, in the sense that they do not give false-positive results.

One of the causes which impairs the sensitivity and especially specificity of these assays is the presence of interferences linked to the sample tested. An interference occurs each time a substance of the sample to be tested produces a reaction which modifies the test signal, thus modifying the correct value of the result, for example by providing a signal which cannot be distinguished from that of the analyte, thus giving false positives, or by attenuating it, thus potentially giving false negatives when the signal is below the detection threshold of the kit used (Tate and Ward, 2004).

In the context of immunological assays, the false-positive reactions are very often associated with nonspecific antigen-antibody reactions due to the presence, in the sample tested, of substances which are interfering with respect to the assay, such as antibodies, which bind to the binding partners used for the assay. For example, the serum of certain patients can contain human antibodies directed against animal proteins, generated for example after vaccination, which are capable of reacting with the animal immunoglobulins that are part of the composition of the assay kit used. They can thus generate aberrant assay results (Kricka, 1999). Interfering endogenous substances may be present both in samples obtained from healthy subjects and in those obtained from subjects who have a pathological condition or who have an infection. The interference phenomenon is independent of the clinical status of the patient.

Various methods for reducing interfering reactions linked to the sample tested have already been described. Thus, for example, it is known practice to use carbohydrate compounds, protein compounds, protein mixtures or hydrolysates (EP 0 260 903; U.S. Pat. No. 4,931,385). The use of modified proteins, and in particular of succinylated or acetylated proteins (EP 0 525 916), or else peptides with sequences of amino acids that are essentially modified with respect to the native sequence, for example peptides consisting essentially of D-(amino acids) (U.S. Pat. No. 6,153,393) has also been described. However, none of these methods makes it possible to completely eliminate the presence of false positives in the assay, and the addition of these substances sometimes even leads to other interferences, reducing the sensitivity of the test.

Other false-positive reactions may be due, not to the sample tested, but to the binding partners themselves used for the test, for instance when it is desired to detect both antigens and antibodies in the same sample, as described in patent application WO 2008/027942. However, these binding-partner-associated interferences are different than those associated with the sample assayed, and the methods used to reduce this type of interference are different than those used to reduce the interferences associated with the sample assayed.

Since not all the interferences are eliminated, laboratories are sometimes obliged to carry out alternative assays or additional measurements in order to verify the result of their diagnostic test. It is therefore most particularly important to have assays in which the interferences have been reduced, or even eliminated, in particular when it is a question of false positives, since the patients will then receive a medication that they do not need.

The Applicant has demonstrated, against all expectations, that, during immunological assaying in the context of the in vitro detection of the presence of a microorganism, it is possible, in order to eliminate the detection of false positives in the samples tested, owing to interferences associated with these samples tested, and without this reducing the sensitivity of the test, to use particular peptides derived from this microorganism, and also peptides which exhibit at least 50% identity with these first peptides, but which are derived from a microorganism different than the microorganism detected.

Indeed, the Applicant has demonstrated that false positives can be associated with the presence of antibodies directed against microorganisms M1 different than the is microorganism M2 to be detected, said microorganisms M1, which are responsible for the interference and the detection of which it is desired to neutralize, exhibiting a certain peptide sequence identity with that of the microorganism M2 to be detected over a limited length, and that the addition of the corresponding particular peptides, belonging to the microorganisms M1 or M2, make it possible to eliminate these false positives without impairing the sensitivity of the test.

Thus, the invention relates to interfering peptides characterized in that their sequence is chosen from:
(i) a peptide sequence S1 of 7 to 12 amino acids originating from the peptide sequence of an antigenic protein of a microorganism M1, and
(ii) a peptide sequence S2 of 7 to 12 amino acids originating from the peptide sequence of a target protein of a microorganism M2 different than the microorganism M1,
it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences.

One subject relates to a method for the in vitro immunoassay-based detection of the presence of a microorganism M2 in a biological sample, by detecting at least one antibody Ab$_{M2}$ directed against a target protein of the microorganism M2 to be detected, characterized in that it comprises the steps of:
- a) providing at least one binding partner for said at least one antibody Ab$_{M2}$ to be detected, required for the immunoassay, said at least one binding partner being derived from said target protein against which the antibody is directed or being the target protein itself,
- b) providing at least one interfering peptide having a sequence chosen from:
  (i) a peptide sequence S1 of 7 to 12 amino acids originating from the peptide sequence of an antigenic protein of a microorganism M1 different than the microorganism M2, and
  (ii) a peptide sequence S2 of 7 to 12 amino acids originating from the peptide sequence of a target protein of said microorganism M2 and being included in the peptide sequence of said at least one binding partner,
  it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences,
- c) carrying out the immunoassay in the presence of said at least one interfering peptide, and
- d) detecting the presence of the microorganism M2 by measuring the complex formed between the antibody Ab$_{M2}$ and the binding partner(s).

Another subject relates to a method for the in vitro immunoassay-based detection of the presence of a microorganism M2 in a biological sample, by detecting at least one target protein of the microorganism M2 to be detected, characterized in that it comprises the steps of:
- a) providing at least one binding partner for said at least one target protein of said microorganism M2, required for the immunoassay,
- b) providing at least one interfering peptide having a sequence chosen from:
  (i) a peptide sequence S1 of 7 to 12 amino acids originating from the peptide sequence of an antigenic protein of a microorganism M1 different than the microorganism M2, and
  (ii) a peptide sequence S2 of 7 to 12 amino acids originating from the peptide sequence of a target protein of said microorganism M2 and being included in the peptide sequence of said at least one target protein,
  it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences,
- c) carrying out the immunoassay in the presence of said at least one interfering peptide, and
- d) detecting the presence of the microorganism M2 by measuring the complex formed between the target protein and the binding partner(s).

Yet another subject relates to the use of an interfering peptide having a sequence chosen from:
(i) a peptide sequence S1 of 7 to 12 amino acids originating from the peptide sequence of an antigenic protein of a microorganism M1, and
(ii) a peptide sequence S2 of 7 to 12 amino acids originating from the peptide sequence of a target protein of a microorganism M2 different than said microorganism M1, it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences, in a method for the in vitro immunoassay-based detection of an analyte representative of said microorganism M2 to be detected, in a biological sample.

Another subject relates to a method for improving the specificity of a method for the in vitro immunoassay-based detection of an analyte representative of a microorganism M2 to be detected, in a biological sample, characterized in that it comprises the use, during the implementation of the immunoassay, of at least one interfering peptide having a sequence chosen from:
(i) a peptide sequence S1 of 7 to 12 amino acids originating from the peptide sequence of an antigenic protein of a microorganism M1 different than the microorganism M2, and
(ii) a peptide sequence S2 of 7 to 12 amino acids originating from the peptide sequence of a target protein of the microorganism M2, it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences.

The Applicant has shown, against all expectations, that the detection of false positives, associated with the sample tested, during the implementation of an immunoassay for the detection of a microorganism M2 can be reduced, or even eliminated, through the use of particular peptides, these peptides having the following characteristics:
- they have a peptide sequence S1 of 7 to 12 amino acids originating from the peptide sequence of an antigenic protein of a microorganism M1 different than the microorganism M2, or they have a peptide sequence S2 of 7 to 12 amino acids originating from the peptide sequence of a target protein of the microorganism M2 to be detected,
- the sequences S1 and S2 are aligned with respect to one another,
- the sequences S1 and S2 exhibit at least 50% identity over their length of 7 to 12 amino acids and at least 4 identical or analogous contiguous amino acids,
- the sequences S1 and S2 have an identical length or they exhibit a difference in length of 1 or 2 amino acids distributed at one and/or the other end of said sequences.

In the interests of clarity, when it is desired to generalize, the interfering peptide which is of use for the purposes of the invention will be referred to as peptide having sequence S, whether this peptide has sequence S1 or S2 and therefore whether it originates from the microorganism M1 or M2. The peptide that was used to isolate the peptide having sequence S will then be referred to as peptide having sequence S', in the knowledge that this choice is entirely arbitrary since the two peptides having sequences S1 and S2, and therefore S and S', are usable and used as interfering peptide according to the invention and therefore that it could have been chosen to refer to the interfering peptide having sequence S1 or S2 as peptide having sequence S'.

In other words, the interfering peptides which are of use for the purposes of the invention are interfering peptides having peptide sequence S, of 7 to 12 amino acids, originating from the peptide sequence of an antigenic protein of a microorganism M, said sequence S being aligned with a different peptide sequence S', of 7 to 12 amino acids, originating from the peptide sequence of a target protein of a microorganism M' different than the microorganism M, it being understood that said sequences S and S' exhibit at least 50% identity over their length of 7 to 12 amino acids and at least 4 identical or analogous contiguous amino acids, that their length is identical or that they exhibit a difference of 1 or 2 amino acids distributed at one or the other end of said sequences.

This peptide having sequence S is particularly useful for neutralizing the sample with respect to the microorganism that it is not desired to detect (M or M'), said microorganism creating interferences with respect to the microorganism to be detected (respectively M' or M). Said microorganism that it is not desired to detect can then be referred to as interfering microorganism.

In other words, when the target microorganism to be detected is the microorganism M, the peptide having sequence S, derived from the target microorganism, serves to neutralize the interfering microorganism M'. On the other hand, when the target microorganism to be detected is the microorganism M', the peptide having sequence S, which is then derived from the interfering microorganism, serves to neutralize the interfering microorganism M.

In the interests of clarity, the microorganism that it is desired to detect will here be denoted microorganism M2, representing a microorganism M' or M, in the knowledge that, of course, this name is arbitrary and it could have been chosen to call this microorganism M1.

In other words, the interfering peptide having sequence S of the invention as defined above is of use for detecting a microorganism M or a microorganism M'.

The microorganisms M2 (M' or M), the presence of which it is desired to detect, are any microorganism which causes a pathological condition and of which it is necessary to carry out a reliable diagnosis in order to implement a treatment or a follow-up or to limit the propagation thereof. The microorganisms may be viruses, bacteria or yeasts, which are well known to those skilled in the art.

By way of nonlimiting examples of viruses, mention may be made of hepatitis viruses, such as hepatitis A, B, C, E and G viruses, human immunodeficiency viruses, such as HIV-1 and HIV-2, Epstein-Barr viruses (EBV), influenza viruses such as H1N1 and H5N1, cytomegalovirus (CMV), measles virus, JC virus, etc.

By way of nonlimiting examples of bacteria, mention may be made of *Staphylococcus*, such as *Staphylococcus aureus, Streptococcus*, such as *Streptococcus pneumoniae*, and *Bacilli.*

By way of nonlimiting examples of yeasts, mention may be made of Candida.

The term "target protein of the microorganism M2" is intended to mean a protein encoded by the genome of said microorganism and produced during infection by said microorganism, which can be detected by means of the immunoassay method, or else which generates an antibody response on the part of the infected host, also detectable by means of the immunoassay method. Thus, for example, in the case of the hepatitis C virus (HCV), the target proteins can be, for example, the Core, NS3, NS4 or NS5 proteins. As regards the HIV-1 virus, mention may be made, for example, of the Env (gp160, gp120, gp41), Gag (p55 and its mature processed forms: the p24 capsid, the p17 matrix, etc.), Pol (reverse transcriptase and integrase), Tat, Nef and Rev proteins. By way of another example, mention may be made of the Emp (extracellular matrix protein-binding protein) or PVL (Panton-Valentine leukocydin) proteins of the *Staphylococcus aureus* bacterium, or the ribosomal small subunit methyltransferase H, elongation factor P or else DnaK chaperone proteins of the *Streptococcus pneumonia* bacterium. Of course, those skilled in the art are entirely aware of the various target proteins of the microorganisms that they wish to detect.

The expression "microorganism M1 (M or M') different than the microorganism M2 (respectively M' or M) to be detected" is intended to mean any microorganism which is not the microorganism M2 itself. The microorganisms M1 and M2 may be microorganisms of the same nature (viruses, bacteria, yeasts) and belonging to the same family (for example the microorganism M2 to be detected may be the HCV virus and the other microorganism is the HBV virus) or belonging to another family (for example, the virus to be detected is the HCV virus and the other microorganism is the HIV-1 virus). The microorganisms M1 and M2 may be microorganisms of different nature (virus/bacterium, virus/yeast, bacterium/yeast). These microorganisms are the microorganisms that each patient may encounter and against which they would develop an antibody response.

According to one embodiment, the microorganism M2 is a virus or a bacterium. According to another embodiment, the microorganism M2 is a virus and the microorganism M1 is a bacterium, or else the microorganism M2 is a bacterium and the microorganism M1 is a virus.

According to one embodiment, the virus is the hepatitis C virus, HCV, and the microorganism different than the virus is a bacterium, in particular chosen from *Staphylococcus aureus, Streptococcus pneumoniae, Bacillus subtilis, Pseudomonas entomophila* and *Pseudomonas putida* (GB-1 strain).

According to another embodiment, the virus is the human immunodeficiency virus, HIV-1, and the microorganism different than the virus is *Mycoplasma pneumoniae.*

The expression "antigenic protein of a microorganism M1 (or interfering microorganism) different than the microorganism M2 to be detected" is intended to mean a protein of said microorganism M1 which induces an antibody response on the part of the infected host, who is also the patient from whom the biological sample is taken. Here again, those skilled in the art know the antigenic proteins of the microorganisms M1 which correspond to the target proteins as described above when it is a question of detection, and they will be able to easily distinguish between proteins of the microorganisms which are antigenic or else referred to as target proteins, and those which are nonantigenic or else referred to as non-target proteins.

Those skilled in the art are also aware that, as previously indicated, the expression "antigenic protein" and the expression "target protein" need to be differentiated only with reference to the microorganism in the detection method, namely with reference to that which it is desired to detect (reference is then made to target protein) or to that which it is desired to neutralize (reference is then made to antigenic protein). It therefore follows that these two terms are used without distinction and are to be understood as being identical for the interfering peptide itself, having sequence S, without reference to its use.

The peptides having sequence S and S', and therefore having sequence S1 or S2, according to the invention have from 7 to 12 amino acids, which corresponds to the amino acid length recognized by a paratope of an antibody. According to one embodiment, the sequences S1 and S2 have from 8 to 10 amino acids.

According to another embodiment, the interfering peptides having sequence S are chosen from:
Y7E-1 having sequence SEQ ID No 1, the peptide having sequence S' being the peptide V7E having sequence SEQ ID No 2,
V7E having sequence SEQ ID No 2, the peptide having sequence S' being the peptide Y7E-1 having sequence SEQ ID No 1,
A8E having sequence SEQ ID No 3, the peptide having sequence S' being the peptide E8E having sequence SEQ ID No 4,
Y7E-2 having sequence SEQ ID No 5, the peptide having sequence S' being the peptide E8E having sequence SEQ ID No 4,
D8E having sequence SEQ ID No 6, the peptide having sequence S' being the peptide E8E having sequence SEQ ID No 4,
E8E having sequence SEQ ID No 4, the peptide having sequence S' being the peptide A8E having sequence SEQ ID No 3 or Y7E-2 having sequence SEQ ID No 5 or D8E having sequence SEQ ID No 6,
E8L-1 having sequence SEQ ID No 7, the peptide having sequence S' being the peptide E8L-2 having sequence SEQ ID No 8, and
E8L-2 having sequence SEQ ID No 8, the peptide having sequence S' being the peptide E8L-1 having sequence SEQ ID No 7.

Among these various peptides, the HCV peptide V7E having sequence SEQ ID No 2 has already been described in patent application EP 0 582 243 A. However, this peptide has not been described as an immunogen. It has never been described as an interfering peptide of use for eliminating the false positives associated with the sample tested. The other peptides are new and constitute a subject of the invention.

Thus, the invention relates to the interfering peptides having a sequence chosen from:
(i) a peptide sequence S1 of 7 to 12 amino acids originating from the peptide sequence of an antigenic protein of a microorganism M1, and
(ii) a peptide sequence S2 of 7 to 12 amino acids originating from the peptide sequence of a target protein of a microorganism M2 different than the microorganism M1,
it being understood that said sequences S1 and S2 are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences, and that the peptide V7E having sequence SEQ ID No 2 is excluded.

In other words, the invention relates to an interfering peptide having sequence S of 7 to 12 amino acids originating from the peptide sequence of an antigenic protein of a microorganism M, said sequence S being aligned with respect to a peptide sequence S', of 7 to 12 amino acids, originating from the peptide sequence of a target protein of a microorganism M' different than the microorganism M, it being understood that said sequences S and S' are aligned with respect to one another, that they exhibit at least 50% identity over their length of 7 to 12 amino acids and at least 4 identical or analogous contiguous amino acids, that their length is identical or that they exhibit a difference of 1 or 2 amino acids distributed at one and/or the other end of said sequences, and that the peptide V7E having sequence SEQ ID No 2 is excluded.

According to one particular embodiment, the invention relates to the following peptides: Y7E-1 having sequence SEQ ID No 1, A8E having sequence SEQ ID No 3, E8E having sequence SEQ ID No 4, Y7E-2 having sequence SEQ ID No 5, D8E having sequence SEQ ID No 6, E8L-1 having sequence SEQ ID No 7 and E8L-2 having sequence SEQ ID No 8.

The term "at least 50% identity" is intended to mean the fact that at least half of the amino acids of each sequence are identical or analogous, it being understood that these two sequences exhibit at least 4 identical or analogous contiguous amino acids.

Generally, the term "analogous amino acid" refers to an amino acid which, when it replaces the native amino acid in the sequence or when it is absent, does not cause any destruction of the antigenic reactivity of said sequence.

The particularly preferred analogs include substitutions which are conservative in nature, i.e. substitutions which take place in an amino acid family. There are several amino acid classifications in terms of family, as well known to those skilled in the art. Thus, according to one classification example, amino acids can be divided up into 4 families, namely (1) acidic amino acids such as aspartate and glutamate, (2) basic amino acids such as lysine, arginine and histidine, (3) nonpolar amino acids such as leucine, isoleucine and methionine, and (4) polar uncharged amino acids such as glycine, asparagine, glutamine, serine, threonine and tyrosine. Phenylalanine, tryptophan and tyrosine are sometimes classified as aromatic amino acids. For example, it can reasonably be predicted that an isolated replacement of leucine with isoleucine or valine, of an aspartate with a glutamate, of a threonine with a serine, or a similar conservative replacement of one amino acid with another amino acid having a structural relationship, would have no major effect on the biological activity. Another example of a method for predicting the effect of an amino acid substitution on the biological activity has been described by Ng and Henikoff, 2001.

The sequences S and S' (S1 and S2) are aligned with respect to one another with an identical length or they exhibit a difference of 1 or 2 amino acids distributed at one and/or the other end of said sequences. In other words, the sequences S and S' (S1 and S2) have a common sequence of at least 7 amino acids, with amino acids which are identical or analogous, by conservative substitution or deletion as previously described, and, when their length is different, the additional amino acids with respect to this common sequence are at one end (1 or 2 amino acids), at the other end (1 or 2 amino acids), or at both ends (1 or 2 amino acids indifferently on each side). Thus, if X is the common sequence, $A_n$ is a difference of amino acid placed at the end and n is an integer from 1 to 4, the alignments of the peptides of the invention can be represented as follows:

| $\underline{X}A_1$ | $A_1\underline{X}$ | $\underline{X}A_1A_2$ | $A_1A_2\underline{X}$ |
| $\underline{X}$ | $\underline{X}$ | $\underline{X}$ | $\underline{X}$ |
| $A_1\underline{X}A_2$ | $A_1A_2\underline{X}A_3$ | $A_1\underline{X}A_2A_3$ | $A_1A_2\underline{X}A_3A_4$ |
| $\underline{X}$ | $\underline{X}$ | $\underline{X}$ | $\underline{X}$ |

The maximum difference of amino acids is therefore 4.

Those skilled in the art will easily determine the regions of the sequence which can tolerate a change without any major effect on the biological activity, with reference to Hopp/Woods and Kyte-Doolite plots, well known to those skilled in the art.

According to one embodiment, the amino acids of the sequence common to the sequences S and S' (S1 and S2) comply with at least one of the following characteristics:

they are identical, if they exhibit analogs, they exhibit at most 1 or 2 analogs, they exhibit at most 3 analogs by conservative substitution, they exhibit at most 1 or 2 analogs by deletion.

According to another embodiment, the at least 4 contiguous amino acids comply with at least one of the following characteristics:

they are identical or analogous by conservative substitution, when they exhibit analogs, there are at most 1 or 2 of the latter.

According to yet another embodiment of the invention, the two sequences S and S' (S1 and S2) exhibit at least 50%, preferably at least 55-60%, more preferably at least 70%, more preferably at least 80-90% sequence identity over the predefined length of the peptide molecules, and also any value above 50% and up to 100%.

The peptides of the invention are particularly useful for reducing, or even eliminating, the false positives of an immunological assay method during the determination of the presence of a microorganism M2 (M' or M) in a biological sample capable of giving false positives, these false positives being caused by the presence of antibodies directed against a microorganism M1 (respectively M or M') different than the microorganism M2 (M' or M) to be detected (which will be referred to as $Ab_{M1}$ or respectively $Ab_M$ or $Ab_{M'}$).

In order to carry out the detection of the presence of the microorganism M2 (M' or M) to be detected, either the detection of at least one antibody directed against a target protein of the microorganism M2 to be detected (which antibody will be referred to as $Ab_{M2}$ or respectively $Ab_{M'}$ or $Ab_M$) will be carried out, or the detection of at least one target protein as previously described will be carried out, or both. Reference is then made, in the latter case, to a combination method or combo method.

When the method for the in vitro immunoassay-based detection of the presence of a microorganism M2 (M' or M) in a biological sample comprises or consists of the detection of at least one antibody $Ab_{M2}$ directed against a target protein of the microorganism M2 to be detected, said method comprises or consists of the steps of:

a) providing at least one binding partner for said at least one antibody $Ab_{M2}$ to be detected, required for the immunoassay, said at least one binding partner being derived from said target protein against which the antibody is directed or being the target protein itself, b) providing at least one interfering peptide as defined above, it being understood that the sequence S1 belongs to the microorganism M1 different than the microorganism M2 to be detected and the sequence S2 is included in the peptide sequence of said at least one binding partner, c) carrying out the immunoassay in the presence of said at least one interfering peptide, and d) detecting the presence of the microorganism M2 by measuring the complex formed between the antibody $Ab_{M2}$ and the binding partner(s).

When the microorganism M2 to be detected is the microorganism to which the peptide having sequence S belongs (it is therefore the microorganism M), the method for the in vitro immunoassay-based detection of the presence of a microorganism M in a biological sample comprises or consists of the detection of at least one antibody $Ab_M$ directed against a target protein of the microorganism M to be detected, said method comprising or consisting of the steps of:

a) providing at least one interfering peptide having peptide sequence S as previously defined, b) providing at least one binding partner for said at least one antibody $Ab_M$ to be detected, required for the immunoassay, said at least one binding partner being derived from said target protein against which the antibody is directed or being the target protein itself, and including the peptide sequence S, c) carrying out the immunoassay in the presence of said at least one interfering peptide having peptide sequence S, and d) detecting the presence of the microorganism M by measuring the complex formed between the antibody $Ab_M$ and the binding partner(s).

When the microorganism M2 to be detected is not the microorganism to which the peptide having sequence S belongs, but the microorganism to which the sequence S' belongs (it is therefore the microorganism M'), the method for the in vitro immunoassay-based detection of the presence of a microorganism M' in a biological sample comprises or consists of the detection of at least one antibody $Ab_{M'}$ directed against a target protein of the microorganism M' to be detected, said method comprising or consisting of the steps of:

a) providing at least one interfering peptide having peptide sequence S as previously defined, b) providing at least one binding partner for said at least one antibody $Ab_{M'}$ to be detected, required for the immunoassay, said at least one binding partner being derived from said target protein against which the antibody is directed or being the target protein itself, and including the peptide sequence S' as previously defined, c) carrying out the immunoassay in the presence of said at least one interfering peptide having peptide sequence S, and d) detecting the presence of the microorganism M' by measuring the complex formed between the antibody $Ab_{M'}$ and the binding partner(s).

The expression "said at least one binding partner being derived from said target protein against which the antibody is directed or being the target protein itself" is intended to mean that the binding partner is the target protein as previously described or else a fragment thereof capable of binding to the antibodies of the sample to be assayed.

When the method for the in vitro immunoassay-based detection of the presence of a microorganism M2 (M' or M) in a biological sample comprises or consists of the detection of at least one target protein of the microorganism M2 to be detected, said method comprises or consists of the steps of:

a) providing at least one binding partner for said at least one target protein of said microorganism M2, required for the immunoassay, b) providing at least one interfering peptide as defined above, it being understood that the sequence S1 belongs to the microorganism M1 different than the microorganism M2 to be detected and the sequence S2 is included in the peptide sequence of said at least one target protein,
c) carrying out the immunoassay in the presence of said at least one interfering peptide, and
d) detecting the presence of the microorganism M2 by measuring the complex formed between the target protein and the binding partner(s).

When the microorganism M2 to be detected is the microorganism to which the peptide having sequence S belongs (it is therefore the microorganism M), the method for the in vitro immunoassay-based detection of the presence of a microorganism M in a biological sample comprises or consists of the detection of at least one target protein of the microorganism M to be detected, said method comprising or consisting of the steps of:
a) providing at least one binding partner for said at least one target protein of said microorganism M, required for the immunoassay,
b) providing at least one interfering peptide having sequence S as defined above, said sequence S being included in the peptide sequence of said at least one target protein,
c) carrying out the immunoassay in the presence of said at least one interfering peptide having sequence S, and
d) detecting the presence of the microorganism M by measuring the complex formed between the target protein and the binding partner(s).

When the microorganism M2 to be detected is not the microorganism to which the peptide having sequence S belongs, but the microorganism to which the sequence S' belongs (it is therefore the microorganism M'), the method for the in vitro immunoassay-based detection of the presence of a microorganism M' in a biological sample comprises or consists of the detection of at least one target protein of the microorganism M' to be detected, said method comprising or consisting of the steps of:
a) providing at least one binding partner for said at least one target protein of said microorganism M', required for the immunoassay,
b) providing at least one interfering peptide having sequence S as defined above, it being understood that the corresponding sequence S' is included in the peptide sequence of said at least one target protein,
c) carrying out the immunoassay in the presence of said at least one interfering peptide having sequence S, and
d) detecting the presence of the microorganism M' by measuring the complex formed between the target protein and the binding partner(s).

By way of binding partner for the target protein to be sought, mention may be made of antibodies, antibody fractions, nanofitins, receptors for this antigen or any other protein which is known to have an interaction with the target protein to be sought.

The binding-partner antibodies are, for example, either polyclonal antibodies or monoclonal antibodies.

The polyclonal antibodies can be obtained by immunization of an animal with the target protein or with the inactivated and/or fractionated viral particle if the microorganism M2 (M' or M) is a virus, or else with a bacterial lysate or an extract of bacterial proteins if the microorganism M2 (M' or M) is a bacterium, followed by the recovery of the desired antibodies in purified form, by taking a serum sample from said animal, and separation of said antibodies from the other serum constituents, in particular by affinity chromatography on a column to which is attached an antigen specifically recognized by the antibodies, in particular said target protein.

The monoclonal antibodies can be obtained by the hybridoma technique, the general principle of which is summarized hereinafter.

Firstly, an animal, generally a mouse, is immunized with the target protein of interest or with the inactivated and/or fractionated viral particle if the microorganism M2 (M' or M) is a virus, or else with a bacterial lysate or an extract of bacterial proteins if the microorganism M2 (M' or M) is a bacterium, and the B lymphocytes of said animal are then capable of producing antibodies against this antigen. These antibody-producing lymphocytes are then fused with "immortal" myeloma cells (murine in the example) so as to give rise to hybridomas. A selection of the cells capable of producing a particular antibody and of indefinitely multiplying is then carried out using the heterogeneous mixture of the cells thus obtained. Each hybridoma is multiplied in the form of a clone, each one resulting in the production of a monoclonal antibody of which the properties of recognition with respect to said target protein may be tested, for example by ELISA, by one-dimensional or two-dimensional immunotransfer (Western blot), by immunofluorescence, or using a biosensor. The monoclonal antibodies thus selected are subsequently purified, in particular according to the affinity chromatography technique described above.

The monoclonal antibodies may also be recombinant antibodies obtained by genetic engineering, using techniques well known to those skilled in the art.

By way of example of antibody fragments, mention may be made of Fab, Fab' and F(ab')$_2$ fragments and also scFv (single chain variable fragment) and dsFv (double-stranded variable fragment) chains. These functional fragments can in particular be obtained by genetic engineering.

Nanofitins (trade name) are small proteins which, like antibodies, are capable of binding to a biological target, thus making it possible to detect it, to capture it or quite simply to target it within an organism.

Regardless of whether a protein and/or an antibody, also referred to as analyte representative of the microorganism M2 (M' or M) to be detected, is detected, the binding partners have in common the fact that they may be specific or nonspecific for the analyte to be detected. They are said to be specific when they are capable of binding exclusively or virtually exclusively to these analytes. They are said to be nonspecific when the selectivity of binding to these analytes is weak and they are then capable of binding to other ligands, such as other proteins or antibodies. According to one preferred embodiment, the specific binding partners are preferred.

These binding partners specific or nonspecific for the analytes sought in the method of the invention can be used as capture reagent, as detection reagent, or as capture and detection reagents in the context of the immunoassay carried out.

Of course, the term "immune" in "immunoassay" for example should not be considered in the present application as strictly indicating that the binding partner is an immunological partner, such as an antibody. Indeed, those skilled in the art also widely use this term when the binding partner, also called ligand, is not an immunological partner but is, for example, a receptor for the analyte that it is designed to assay. Thus, it is common practice to refer to the ELISA assay (Enzyme-Linked Immunosorbent Assay) for assays which use non-immunological binding partners, also broadly referred to as "Ligand Binding Assays", even though the term "immune" is included in the acronym ELISA. In the interests of clarity, the Applicant will use, throughout the application, the term "immune" for any assay using a binding partner, even when it is not an immunological partner.

The implementation of the immunoassay is a step widely known to those skilled in the art who adapt their test according to the microorganism M2 (M' or M) to be detected and the binding partners to be used.

During this method, one or more peptides of the invention will be added and those skilled in the art will adapt the conditions of the test accordingly. The immunoassay method will preferably comprise the use of one, two, three or four interfering peptides according to the invention.

The interfering peptide(s) will be added to the biological sample to be assayed before beginning the immunoassay or in any one of the antigen-antibody reaction steps of the immunoassay. In the case of a one-step immunoassay, the interfering peptides will be present or will be added when the biological sample reacts with the capture phase. In the case of a two-step immunoassay, the interfering peptides will be added during the capture or during the revealing, or both. In any event, the interfering peptides will be added before the revealing step (addition of the substrate and visualization or detection of the signal).

The detection of the presence of the microorganism M2 (M' or M) by measuring the complex formed between the analyte and the binding partners can be carried out by means of any method of visualization of an immunoassay known to those skilled in the art, such as direct or indirect means.

In the case of direct detection, i.e. detection not carried out by means of labeling, the immunological reactions are observed, for example, by surface plasmon resonance or by cyclic voltammetry on an electrode bearing a conductive polymer.

Indirect detection is carried out by means of labeling, either of the binding partner termed detection reagent, or of the target protein itself or of one or more of its fragments.

The term "labeling" is intended to mean the attachment of a label reagent capable of directly or indirectly generating a detectable signal. A nonlimiting list of these label reagents consists of:

- enzymes which produce a signal that is detectable for example by colorimetry, fluorescence or luminescence, for instance horseradish peroxidase, alkaline phosphatase, β-galactosidase or glucose-6-phosphate dehydrogenase,
- chromophores, for instance fluorescent, luminescent or dye compounds,
- radioactive molecules, for instance $^{32}P$, $^{35}S$ or $^{125}I$, and
- fluorescent molecules, such as the Alexas or phycocyanins.

Indirect detection systems can also be used, for instance ligands capable of reacting with an anti-ligand. Ligand/anti-ligand pairs are well known to those skilled in the art, which is the case, for example, with the following pairs: biotin/streptavidin, hapten/antibody, antigen/antibody, peptide/antibody, sugar/lectin, polynucleotide/sequence complementary to the polynucleotide. In this case, it is the ligand which carries the binding partner. The anti-ligand can be directly detectable using the label reagents described in the previous paragraph or can itself be detectable using a ligand/anti-ligand.

These indirect detection systems can, under certain conditions, result in an amplification of the signal. This signal amplification technique is well known to those skilled in the art, and reference may be made to the prior patent applications FR 98/10084 or WO-A-95/08000 by the Applicant or the article by Chevalier et al., 1997.

According to the type of labeling used, those skilled in the art will add reagents which allow the visualization of the labeling or the emission of a signal that is detectable using any type of measuring apparatus, for instance a spectrophotometer, a spectrofluorimeter or else a high-definition camera.

The biological sample in which the method of the invention can be carried out is any biological sample capable of containing an analyte representative of a microorganism (antigen, antibody), in which an immunoassay can be carried out. These samples are widely known to those skilled in the art. By way of example of such samples, mention may be made of biological fluids such as serum, plasma, blood, whole blood, urine or cerebrospinal fluid, but also tissue, stools or the like. The biological samples come from any animal for which it is necessary to detect the presence of a pathogenic microorganism, such as mammals, including human beings, the ovine race, cattle, members of the goat family, members of the canine family, fish and avian species. The Applicant has shown, against all expectations, that these samples are also capable of containing antibodies $Ab_{M1}$ directed against a microorganism different than the microorganism M2 to be detected and that it is these antibodies which produce false-positive results of the test.

The biological sample can be treated in a prior step. For example, acidic conditions, which promote the exposure of the antigens to be detected, can be used. Detergents of ionic or nonionic type, for example triton X100 or SDS (sodium dodecyl sulfate) or poly(oxyethylene) derivatives, for instance NP40, can be used.

The use of the peptides of the invention is therefore particularly useful in any immunoassay methods. Thus, another subject of the invention relates to the use of an interfering peptide having sequence S as defined above, in a method for the in vitro immunoassay-based detection of an analyte representative of a microorganism to be detected, in a biological sample.

Since the usefulness of the peptides of the invention lies in the elimination of the false positives, thus improving the specificity of a test, another subject relates to a method for improving the specificity of a method for the in vitro immunoassay-based detection of an analyte representative of a microorganism to be detected, in a biological sample, characterized in that it comprises the use, during the implementation of the immunoassay, of at least one interfering peptide having sequence S as defined above.

The invention will be understood more clearly by means of the following examples which are given by way of nonlimiting illustration, and also by means of FIGS. 1 to 4, in which:

FIG. 1 shows the alignment between the HCV peptide V7E-1 and the *Staphylococcus aureus* peptide Y7E-1, FIG. 2 shows the alignment between the HCV peptide E8E and the *Streptococcus pneumoniae* peptide A8E (FIG. 2A), the *Bacillus subtilis* peptide Y7E-2 (FIG. 2B) and the *Pseudomonas entomophila* or *Pseudomonas putida* (GB-1 strain) peptide D8E (FIG. 2C), FIG. 3 shows the alignment between the HIV-1 peptide E8L-2 and the *Mycoplasma pneumoniae* peptide E8L-1, and FIG. 4 shows the alignment between the HCV peptide E8E and the *Streptococcus pneumoniae* peptide A6M.

In the figures, "." represents an amino acid identity with respect to the amino acid present in the position above, and "–°" represents a deletion on a given position.

EXAMPLE 1

Interfering Peptides Y7E-1 (*Staphylococcus aureus*) and V7E (HCV)

In order to improve the specificity of the immunoassays for diagnosing an infection with HCV or with *Staphylococcus aureus*, two interfering peptides according to the invention were defined.

The peptide Y7E-1 has the peptide sequence YSPTHYVPE (SEQ ID No 1), which corresponds to amino acids 322-330 of the *Staphylococcus aureus* extracellular matrix protein-binding protein Emp (accession number Q8NXI8 of the UniProtKB database). This peptide Y7E aligns with the HCV peptide V7E, the peptide sequence of which is VSPTHYVPE (SEQ ID No 2) and which corresponds to amino acids 218-226 of the NS4B protein of HCV (numbering according to the NCBI RefSeq reference sequence, the accession number is NP_751926).

The alignment of the peptides Y7E-1 and V7E is shown in FIG. 1. The peptides Y7E-1 and V7E have an identity of 89% for a common length of 9 amino acids.

EXAMPLE 2

Interfering Peptides E8E (HCV) and A8E (*Streptococcus pneumoniae*), Y7E-2 (*Bacillus subtilis*) and D8E (*Pseudomonas entomophila* or *Putida* GB-1 Strain)

In order to improve the specificity of the immunoassays for diagnosing an infection with HCV, *Streptococcus pneumoniae*, *Bacillus subtilis* or *Pseudomonas entomophila* or *putida* GB-1 strain, several interfering peptides according to the invention were defined.

The peptide A8E has the peptide sequence AQKRLAPYIE (SEQ ID No 3), which corresponds to amino acids 64-73 of the *Streptococcus pneumoniae* ribosomal small subunit methyltransferase H protein (accession number C1CPL0 of the UniProtKB database). This peptide aligns with the HCV peptide E8E, the peptide sequence of which is ECSQHLPYIE (SEQ ID No 4) and which corresponds to amino acids 53-54 of the NS4A protein of HCV (NP_751925), fused to amino acids 1-8 of the NS4B protein of HCV (NP_751926). The alignment of the peptides A8E and E8E is shown in FIG. 2A. The peptides A8E and E8E have an identity of 50% for a common length of 10 amino acids.

Peptides of microorganisms other than *Streptococcus pneumoniae* can also be aligned with the HCV peptide E8E of the invention. The peptide Y7E-2 has the peptide sequence YFQHIPYLE (SEQ ID No 5), which corresponds to amino acids 84-92 of the *Bacillus subtilis* methionine-binding lipoprotein metQ (accession number O32167 of the UniProtKB database). The alignment of the peptides Y7E-2 and E8E is shown in FIG. 2B. The peptides Y7E-2 and E8E have an identity of 55% for a common length of 9 amino acids.

The peptide D8E has the peptide sequence DIDAVLPYIE (SEQ ID No 6), which corresponds to amino acids 97-106 of the elongation factor P protein of *Pseudomonas entomophila* (accession number Q11D35 of the UniProtKB database) and of *Pseudomonas putida* (GB-1 strain) (accession number B0KUN5 of the UniProtKB database). The alignment of the peptides D8E and E8E is shown in FIG. 2C.

The peptides D8E and E8E have an identity of 50% for a common length of 10 amino acids.

EXAMPLE 3

Interfering Peptides E8L-1 (*Mycoplasma pneumoniae*) and E8L-2 (HIV-1)

In order to improve the specificity of the immunoassays for diagnosing an infection with HIV-1 or with *Mycoplasma pneumoniae*, interfering peptides according to the invention were defined.

The peptide E8L-1 has the peptide sequence EAYRKEQQLL (SEQ ID No 7), which corresponds to amino acids 200-209 of the *Mycoplasma pneumoniae* M129 tRNA (guanine-N(1)-)-methyltransferase protein (accession number P75132 of the UniProtKB database). This peptide aligns with the HIV-1 peptide E8L-2, the peptide sequence of which is ERYLKDQQLL (SEQ ID No 8) and which corresponds to amino acids 584-593 of the gp160 envelope glycoprotein of HIV-1 (numbering according to the NCBI RefSeq reference sequence, the accession number is NP_057856). The exact position can vary from one HIV-1 strain to another, given the great genetic variability of this virus. The alignment of the peptides E8L-1 and E8L-2 is shown in FIG. 3. The peptides E8L-1 and E8L-2 have an identity of 70% for a length of 10 amino acids.

EXAMPLE 4

Improvement of the Specificity of an Immunoassay for Anti-HCV Antibodies Through the Use of Interfering Peptides According to the Invention The diagnosis of a hepatitis C virus infection is currently carried out using immunoassays which are $3^{rd}$-generation immunoenzymatic serological tests and which demonstrate antibodies directed against the proteins Core, NS3, and NS4, and NS5 for certain tests. These detected anti-HCV antibodies are evidence of a current or past infection.

The immunoenzymatic serological tests which make it possible to demonstrate anti-virus antibodies can be carried out in a microplate, in an automated manner or manually, or else using automated immunoanalysis devices such as Vidas® (bioMérieux). In this case, all the steps of the test are carried out automatically by the instrument. The various immunoenzymatic techniques, and in particular ELISA, are well known by those skilled in the art and the major principles and also protocol examples are described in the book "The ELISA Guidebook", second edition, by John R. Crowther, published by Humana Press (DOI: 10.1007/978-1-60327-254-4).

The disposable tip (SPR®) acts both as a solid phase and as a pipetting system. The surface of the tip is coated with antigens for the detection of antibodies directed against the HCV Core, NS3 and NS4 proteins. In a first step, the sample is diluted, and then suctioned up and down inside the tip. The anti-HCV antibodies present in the sample will bind to the antigens present inside the tip. Washing steps remove the unbound compounds. During the second step, (mouse) anti-human immunoglobulin (anti-IgG) monoclonal IgGs in Fab' form, conjugated to recombinant alkaline phosphatase, are suctioned up and down inside the tip and will bind to the anti-HCV human Igs from the sample tested, bound to the antigens of the solid phase. Washing steps again remove the unbound compounds. During the final revealing step, the substrate (4-methylumbelliferyl phosphate) is suctioned up and down in the tip; the enzyme of the conjugate catalyzes the reaction for hydrolysis of this substrate to give a product (4-methylumbelliferone), the emitted fluorescence of which is measured at 450 nm. The value of the fluorescence signal is proportional to the concentration of the antibody present in the sample. At the end of the test, the results are calculated automatically in the form of an index by the instrument, by dividing the value obtained by the value of the standard S1 brought back to 1 (value stored in the instrument). Thus, a sample of which the index is greater than or equal to 1 is considered to be positive by the immunoenzymatic test (presence of anti-HCV antibodies) and a sample of which the index is less than 1 is considered to be negative (absence of anti-HCV antibodies). In the paragraphs which follow, this HCV-antibody assay procedure will be referred to as "Operating Mode 1", which corresponds to the assaying of anti-HCV antibodies without interfering peptide.

In order to reduce the interferences associated with non-specific recognition of antigens of Operating Mode 1 for the detection of anti-NS4 antibodies, owing to the elements contained in the samples tested, various interfering peptides defined in examples 1 and 2 were used. They are peptides which belong either to the virus to be detected (use of a peptide having sequence S of the invention for the detection of a microorganism M), or to a microorganism different than the virus to be detected (use of a peptide having sequence S of the invention for the detection of a microorganism M'). These peptides were produced by chemical synthesis according to procedures well known to those skilled in the art, such as solid-phase peptide synthesis described by Merrifield, 1962 and Fields and Noble, 1990, using a polymer of polystyrene type containing 0.1-1.0 mmol amines/g of polymer. At the end of the chemical synthesis, the peptides can be deprotected and cleaved from the polymer in the presence of a trifluoroacetic acid-ethanedithiol-triisopropylsilane-water (94/2.5/1/2.5 V/V/V/V) mixture for approximately two hours. After elimination of the polymer, the peptides are extracted by precipitation from diethyl ether at 0° C. They can be purified by techniques such as high performance liquid chromatography. Lyophilization of the appropriate purification fractions results in a homogenous peptide which may be characterized by standard physico-chemical techniques such as mass spectrometry, high performance liquid chromatography or amino acid analysis.

Several hundred serum samples, negative for HCV infection and originating from the Rhône-Alpes "Centres de Transfusion Sanguine" [Blood Banks], were screened in order to identify the samples which posed an interference problem. To do this, the samples were assayed according to Operating Mode 1 using the Vidas automated device. Only the sera that were positive according to Operating Mode 1 (index ≥1) were selected.

Such a difference between the result of Operating Mode 1 and that of the negative status established by the "Centres de Transfusion Sanguine" [Blood Banks] makes it possible to select the false-positive sera posing an interference problem.

In order to show that the use of interfering peptides according to the invention does not impair the sensitivity of the test, a positive control sample C1 derived from a commercial serum pool (Trina Bioreactives AG) was also assayed.

Table 1 gives, for seven sera posing an interference problem and for the positive control C1, the results of assays carried out according to "Operating Mode 1" with or without the presence of the peptide V7E (SEQ ID No 2) or of the peptide Y7E (SEQ ID No 1). These peptides were added at a concentration of 5 µg/ml during the first step of the immunoenzymatic test protocol which corresponds to the dilution of the sample to be tested and the incubation thereof with the antigens present on the solid phase.

TABLE 1

|  | Operating Mode 1 | Operating Mode 1 + V7E pos indices ≥1 | Operating Mode 1 + Y7E |
|---|---|---|---|
| Samples with interference | | | |
| 175 1811 | 1.44 | 0.49 | 0.47 |
| 498 | 1.65 | 0.35 | 0.14 |
| F53 3009 | 1.19 | 0.39 | 0.32 |
| M43 | 1.73 | 0.42 | 0.17 |
| H48 | 7.12 | 1.17 | 0.88 |
| 801 1409 | 1.91 | 1.04 | 0.71 |
| 284 2408 | 2.33 | 1.51 | 0.86 |
| Positive control | | | |
| C1 | 3.02 | 3.06 | 3.02 |

The addition of the peptide Y7E during the assay makes it possible to totally neutralize the interference in all the sera. The peptide V7E makes it possible, for its part, to neutralize the interference in 4/7 of the sera. Furthermore, the sensitivity of the test is not impaired with the use of the interfering peptides.

Likewise, table 2 gives, for two other sera posing an interference problem and for the positive control, the results of assays carried out according to Operating Mode 1 of the anti-HCV antibody detection protocol, with or without the presence of the peptide E8E (SEQ ID No 4), of the peptide A8E (SEQ ID No 3), or else of the peptide A6M (SEQ ID No 9). These peptides were added at a concentration of 1 µg/ml during the first step of the immunoenzymatic test protocol, which corresponds to the dilution of the sample to be tested, and the incubation thereof with the antigens present on the solid phase.

The peptide A6M, the peptide sequence of which is APYIEKGM (SEQ ID No 9), is also a *Streptococcus pneumoniae* peptide which corresponds to amino acids 69-76 of the ribosomal small subunit methyltransferase H protein (accession number C1CPL0 of the UniProtKB database). This peptide is not an interfering peptide according to the invention since it does not correspond to the definition of the alignment as claimed (see FIG. 4). Indeed, even though this peptide has 4 contiguous amino acids identical to the HCV peptide E8E and is 8 amino acids long, its sequence is not aligned with respect to that of E8E. In this respect, this peptide A6M is used as a negative control in the experiment shown in table 2.

TABLE 2

|  | Operating Mode 1 Index | Operating Mode 1 + E8E Index | Operating Mode 1 + A8E Index | Operating Mode 1 + A6M Index |
|---|---|---|---|---|
| Samples with interference | | | | |
| F25 | 4.32 | 0.85 | 0.41 | 2.90 |
| 295 | 1.02 | 0.90 | 0.95 | 1.04 |
| Positive control | pos indices ≥1 | | | |
| C1 | 3.03 | 2.92 | 3.02 | 3.05 |

The addition of the peptide E8E or else of the peptide A8E during the assay makes it possible to totally neutralize the interference in 2/2 of the sera. The peptide A6M, which is not a peptide according to the invention, does not make it possible to neutralize the interference, in any of the sera. Here again, the sensitivity of the test is not impaired.

LITERATURE REFERENCES

Chevalier et al., 1997, J Histochem Cytochem, 45, 481-491
Kricka L T, 1999, *Clinical Chemistry* 45(7): 942-956
Fields G B, Noble R L., 1990, Int J Pept Protein Res., 35(3):161-214
Merrifield, 1962, J. Am. Chem. Soc. 85:2149
Ng and Henikoff, 2001, Genome Res 11: 863-874
Tate J and Ward G, 2004, Clin Biochem Rev, 25: 105-120

The invention claimed is:

1. A method for in vitro detection of a microorganism M using a biological sample comprising:

performing an immunoassay that includes contacting the biological sample with an interfering peptide and a binding partner for (i) an antibody $Ab_M$ directed against a target protein of the microorganism M, or (ii) the target protein of the microorganism M; and determining whether a complex has formed between the binding partner and (i) the antibody $Ab_M$, or (ii) the target protein;

wherein:

formation of the complex indicates that the microorganism M is present;

the interfering peptide has a peptide sequence S of 7 to 12 amino acids that is included in the peptide sequence of the target protein of the microorganism M;

the sequence S is aligned with respect to a peptide sequence S' of 7 to 12 amino acids that is included in the peptide sequence of an antigenic protein of an interfering microorganism M' different from the target microorganism M;

the sequences S and S' exhibit at least 50% identity over their length of 7 to 12 amino acids and at least 4 identical or analogous contiguous amino acids;

the sequences S and S' have identical lengths or exhibit a difference of 1 or 2 amino acids distributed at one and/or the other end of the sequences;

the interfering peptide blocks false positive results linked to the presence of antibodies $Ab_{M'}$ directed against the antigenic protein of the interfering microorganism M'; and one of the microorganism M and the microorganism M' is hepatitis C virus (HCV) and the other of the microorganism M and the microorganism M' is selected from the group consisting of *Staphylococcus aureus, Streptococcus pneumoniae, Bacillus subtilis, Pseudomonas entomophila*, and *Pseudomonas putida* (GB-1 strain); or one of the microorganism M and the microorganism M' is human immunodeficiency virus HIV-1 and the other of the microorganism M and the microorganism M' is *Mycoplasma pneumoniae.*

2. A method for in vitro detection of a microorganism M' using a biological sample comprising:

performing an immunoassay that includes contacting the biological sample with an interfering peptide and a binding partner for (i) an antibody $Ab_{M'}$ directed against a target protein of the microorganism M', or (ii) the target protein of the microorganism M'; and determining whether a complex has formed between the binding partner and (i) the antibody $Ab_{M'}$, or (ii) the target protein;

wherein:

formation of the complex indicates that the microorganism M' is present;

the interfering peptide has a peptide sequence S of 7 to 12 amino acids that is included in the peptide sequence of an antigenic protein of an interfering microorganism M different than the microorganism M';

the sequence S is aligned with respect to a peptide sequence S' of 7 to 12 amino acids that is included in the peptide sequence of the target protein of the microorganism M';

the sequences S and S' exhibit at least 50% identity over their length of 7 to 12 amino acids and at least 4 identical or analogous contiguous amino acids;

the sequences S and S' have identical lengths or exhibit a difference of 1 or 2 amino acids distributed at one and/or the other end of the sequences;

the interfering peptide blocks false positive results linked to the presence of antibodies $Ab_M$ directed against the antigenic protein of the interfering microorganism M; and one of the microorganism M' and the microorganism M is hepatitis C virus (HCV) and the other of the microorganism M' and the microorganism M is selected from the group consisting of *Staphylococcus aureus, Streptococcus pneumoniae, Bacillus subtilis, Pseudomonas entomophila*, and *Pseudomonas putida* (GB-1 strain); or one of the microorganism M' and the microorganism M is human immunodeficiency virus HIV-1 and the other of the microorganism M' and the microorganism M is *Mycoplasma pneumoniae*.

3. The method according to claim 1, wherein the sequences S and S' have from 8 to 10 amino acids.

4. The method according to claim 2, wherein the sequences S and S' have from 8 to 10 amino acids.

5. The method according to claim 1, wherein the microorganism M is the hepatitis C virus (HCV), and the microorganism M' is selected from the group consisting of *Staphylococcus aureus, Streptococcus pneumoniae, Bacillus subtilis, Pseudomonas entomophila*, and *Pseudomonas putida* (GB-1 strain).

6. The method according to claim 2, wherein the microorganism M' is the hepatitis C virus (HCV), and the microorganism M is selected from the group consisting of *Staphylococcus aureus, Streptococcus pneumoniae, Bacillus subtilis, Pseudomonas entomophila*, and *Pseudomonas putida* (GB-1 strain).

7. The method according to claim 1, wherein the peptide having sequence S is selected from the group consisting of Y7E-1 having sequence SEQ ID NO. 1, A8E having sequence SEQ ID NO. 3, Y7E-2 having sequence SEQ ID NO. 5, D8E having sequence SEQ ID NO. 6, and E8E having sequence SEQ ID NO. 4.

8. The method according to claim 2, wherein the peptide having sequence S is selected from the group consisting of Y7E-1 having sequence SEQ ID NO. 1, A8E having sequence SEQ ID NO. 3, Y7E-2 having sequence SEQ ID NO. 5, D8E having sequence SEQ ID NO. 6, and E8E having sequence SEQ ID NO. 4.

9. The method according to claim 1, wherein the microorganism M is the human immunodeficiency virus HIV-1, and the microorganism M' is *Mycoplasma pneumoniae*.

10. The method according to claim 2, wherein the microorganism M' is the human immunodeficiency virus HIV-1, and the microorganism M is *Mycoplasma pneumoniae*.

11. The method according to claim 1, wherein the peptide having sequence S is selected from the group consisting of E8L-1 having sequence SEQ ID NO. 7 and E8L-2 having sequence SEQ ID NO. 8.

12. The method according to claim 2, wherein the peptide having sequence S is selected from the group consisting of E8L-1 having sequence SEQ ID NO. 7 and E8L-2 having sequence SEQ ID NO. 8.

13. The method according to claim 1, wherein the interfering peptide is not the peptide V7E having sequence SEQ ID NO. 2.

14. The method according to claim 1, wherein the binding partner is derived from the target protein against which the antibody $Ab_M$ is directed or the binding partner is the target protein; and the binding partner includes the peptide sequence S.

15. The method according to claim 2, wherein the interfering peptide is not the peptide V7E having sequence SEQ ID NO. 2.

16. The method according to claim 2, wherein the binding partner is derived from the target protein against which the antibody $Ab_{M'}$ is directed or the binding partner is the target protein; and the binding partner includes the peptide sequence S'.

17. The method according to claim 1, wherein the microorganism M is selected from the group consisting of *Staphylococcus aureus, Streptococcus pneumoniae, Bacillus subtilis, Pseudomonas entomophila*, and *Pseudomonas putida* (GB-1 strain); and the microorganism M' is hepatitis C virus (HCV).

18. The method according to claim 2, wherein the microorganism M is hepatitis C virus (HCV), and the microorganism M' is selected from the group consisting of *Staphylococcus aureus, Streptococcus pneumoniae, Bacillus subtilis, Pseudomonas entomophila*, and *Pseudomonas putida* (GB-1 strain).

19. The method according to claim 1, wherein the microorganism M is *Mycoplasma pneumoniae*, and the microorganism M' is the human immunodeficiency virus HIV-1.

20. The method according to claim 2, wherein the microorganism M is the human immunodeficiency virus HIV-1, and the microorganism M' is *Mycoplasma pneumoniae*.

* * * * *

```
                               SEQUENCE LISTING

<160> NUMBER OF SEQ ID NOS: 9

<210> SEQ ID NO 1
   <211> LENGTH: 9
   <212> TYPE: PRT
   <213> ORGANISM: staphylococcus

<400> SEQUENCE: 1

Tyr Ser Pro Thr His Tyr Val Pro Glu
   1               5

<210> SEQ ID NO 2
   <211> LENGTH: 9
   <212> TYPE: PRT
   <213> ORGANISM: HCV

<400> SEQUENCE: 2

Val Ser Pro Thr His Tyr Val Pro Glu
   1               5

<210> SEQ ID NO 3
   <211> LENGTH: 10
   <212> TYPE: PRT
   <213> ORGANISM: Streptoccus

<400> SEQUENCE: 3

Ala Gln Lys Arg Leu Ala Pro Tyr Ile Glu
   1               5                   10

<210> SEQ ID NO 4
   <211> LENGTH: 10
   <212> TYPE: PRT
   <213> ORGANISM: HCV

<400> SEQUENCE: 4

Glu Cys Ser Gln His Leu Pro Tyr Ile Glu
   1               5                   10

<210> SEQ ID NO 5
   <211> LENGTH: 9
   <212> TYPE: PRT
   <213> ORGANISM: Bacillus

<400> SEQUENCE: 5

Tyr Phe Gln His Ile Pro Tyr Leu Glu
   1               5

<210> SEQ ID NO 6
   <211> LENGTH: 10
   <212> TYPE: PRT
   <213> ORGANISM: Pseudomonas

<400> SEQUENCE: 6

Asp Ile Asp Ala Val Leu Pro Tyr Ile Glu
   1               5                   10

<210> SEQ ID NO 7
```

-continued

```
<211> LENGTH: 10
<212> TYPE: PRT
<213> ORGANISM: Mycoplasma

<400> SEQUENCE: 7

Glu Ala Tyr Arg Lys Glu Gln Gln Leu Leu
1               5                   10

<210> SEQ ID NO 8
<211> LENGTH: 10
<212> TYPE: PRT
<213> ORGANISM: HIV

<400> SEQUENCE: 8

Glu Arg Tyr Leu Lys Asp Gln Gln Leu Leu
1               5                   10

<210> SEQ ID NO 9
<211> LENGTH: 8
<212> TYPE: PRT
<213> ORGANISM: Streptococcus

<400> SEQUENCE: 9

Ala Pro Tyr Ile Glu Lys Gly Met
1               5
```